US008966687B2

(12) United States Patent
Wilson et al.

(10) Patent No.: US 8,966,687 B2
(45) Date of Patent: Mar. 3, 2015

(54) JOINT ASSEMBLY FOR CONNECTING A LONG EXTENSION PANEL TO A PATIENT SUPPORT PANEL OF A RADIATION THERAPY TABLE AND A TWO-PIECE PATIENT SUPPORT TABLE FORMED THEREBY

(75) Inventors: Roger F. Wilson, Sarasota, FL (US);
Charles Klasson, Boulder, CO (US);
Bruce Ribble, Swisher, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 10 days.

(21) Appl. No.: 13/477,433

(22) Filed: May 22, 2012

(65) Prior Publication Data

US 2013/0312184 A1    Nov. 28, 2013

(51) Int. Cl.
  *A47B 7/00*   (2006.01)
  *A47B 13/00*  (2006.01)
  *A47B 1/00*   (2006.01)

(52) U.S. Cl.
  USPC ..................... 5/613; 5/601; 108/65

(58) Field of Classification Search
  CPC .... A61B 6/0442; A61G 2210/50; A47B 1/00; A47B 87/002
  USPC ......... 5/601, 613, 621, 661, 507.1, 84.1, 658; 108/64, 65, 90; 403/353, 321, 322.1, 403/322.4, 326
  See application file for complete search history.

(56) References Cited

U.S. PATENT DOCUMENTS

| | | | |
|---|---|---|---|
| 3,695,189 A * | 10/1972 | Felder, Jr. ..................... | 108/65 |
| 4,915,034 A * | 4/1990 | Grabe et al. ................... | 108/65 |
| 5,588,771 A * | 12/1996 | Scott et al. .................... | 403/353 |
| 5,661,859 A | 9/1997 | Schaefer | |
| 5,675,851 A | 10/1997 | Feathers | |
| 5,678,948 A * | 10/1997 | White ........................... | 403/321 |
| 6,199,233 B1 | 3/2001 | Kantrowitz et al. | |
| 6,557,195 B2 | 5/2003 | Dinkler | |
| 6,598,275 B1 * | 7/2003 | Kolody et al. ................. | 24/455 |
| 6,640,364 B1 * | 11/2003 | Josephson et al. ............ | 5/601 |
| 6,832,400 B2 * | 12/2004 | Loveday et al. ............... | 5/601 |

(Continued)

FOREIGN PATENT DOCUMENTS

DE    92 14 382 U1    2/1993
DE    102 28 839 C1    10/2003

(Continued)

OTHER PUBLICATIONS

International Search Report for PCT/US2013/041978 mailed Aug. 21, 2013.

*Primary Examiner* — Nicholas Polito
*Assistant Examiner* — Eric Kurilla
(74) *Attorney, Agent, or Firm* — Caesar, Rivise, Bernstein, Cohen & Pokotilow, Ltd.

(57) ABSTRACT

A joint assembly for forming a two part radiation therapy treatment table is disclosed. The treatment table includes a patient support panel to which one portion of the joint assembly is secured, and a table extension panel to which another portion of the joint assembly is secured. The joint assembly self-aligns, self levels, is immediately stable, and locks automatically by its weight and downward pressure. The joint assembly also includes an automatic failsafe secondary lock that resists joint release if upward forces are applied. Disengaging the secondary lock requires and results in no displacement of the two panels. Upon separation of the two panels the lock resets automatically.

24 Claims, 16 Drawing Sheets

(56) References Cited

U.S. PATENT DOCUMENTS

| | | | |
|---|---|---|---|
| 6,912,959 B2 | 7/2005 | Kolody et al. | |
| 6,928,676 B1 * | 8/2005 | Schwaegerle | 5/622 |
| 6,941,599 B2 | 9/2005 | Zacharopoulos et al. | |
| 7,020,917 B1 * | 4/2006 | Kolody et al. | 5/621 |
| 7,076,821 B2 | 7/2006 | de Mooy | |
| 7,272,866 B1 * | 9/2007 | Bradcovich | 5/601 |
| 7,540,661 B2 | 6/2009 | Hornig | |
| 2003/0205176 A1 * | 11/2003 | Kolody et al. | 108/28 |
| 2005/0081295 A1 | 4/2005 | Malcolm | |
| 2007/0214570 A1 | 9/2007 | Coppens et al. | |
| 2009/0308400 A1 | 12/2009 | Wilson et al. | |
| 2010/0251483 A1 * | 10/2010 | Shimada et al. | 5/613 |

FOREIGN PATENT DOCUMENTS

| | | | |
|---|---|---|---|
| DE | 20 2008 016701 U1 | 4/2010 | |
| GB | 2100121 A * | 12/1982 | A47B 1/00 |
| GB | 2 405 789 A | 3/2005 | |
| WO | 2005004723 A1 | 1/2005 | |
| WO | 2006/034914 A1 | 4/2006 | |
| WO | 2009029524 A1 | 3/2009 | |

* cited by examiner

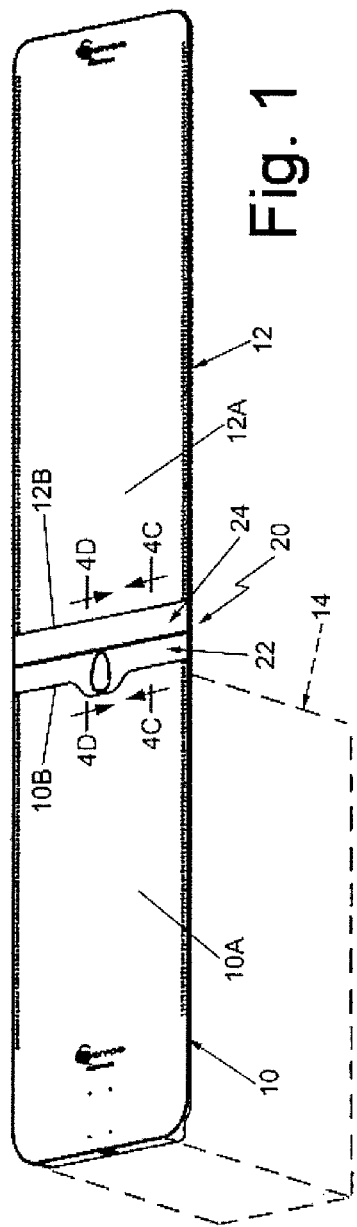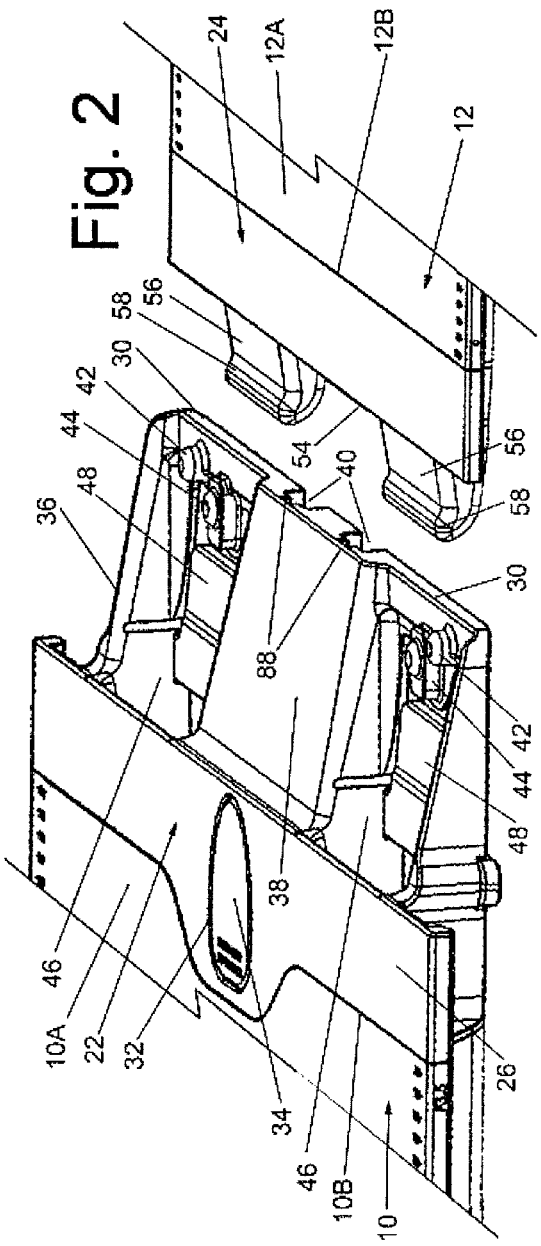

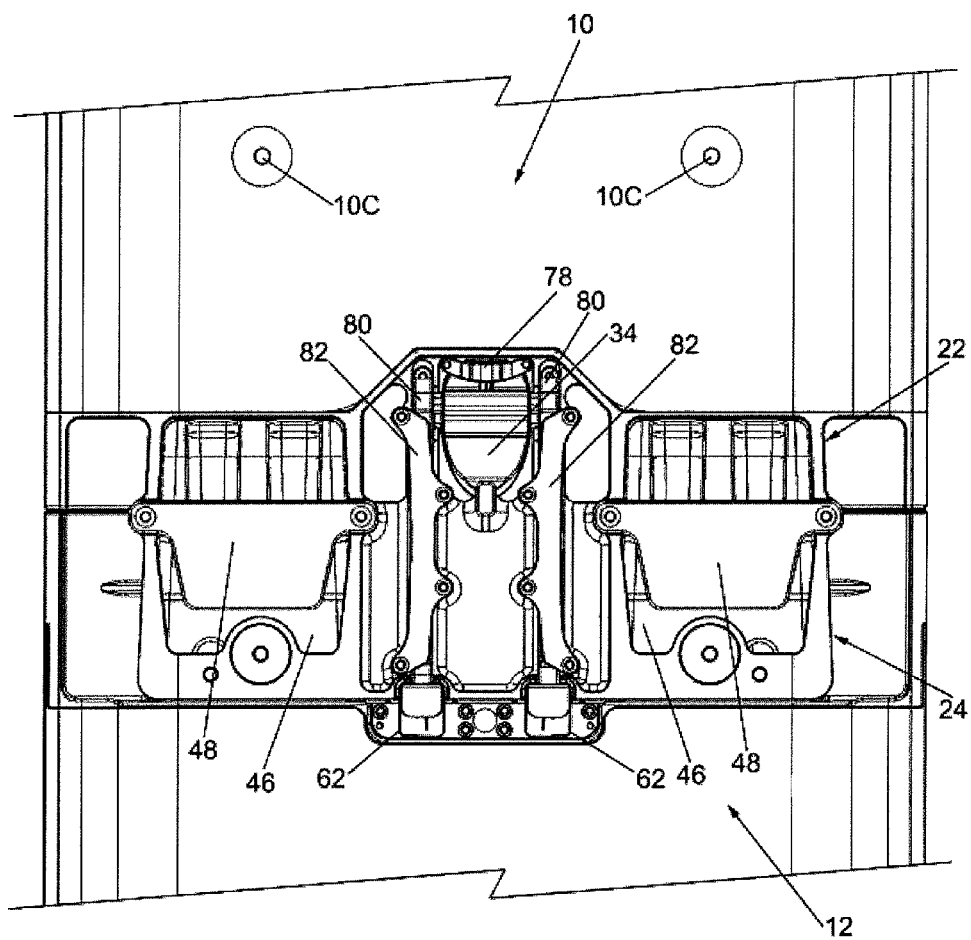

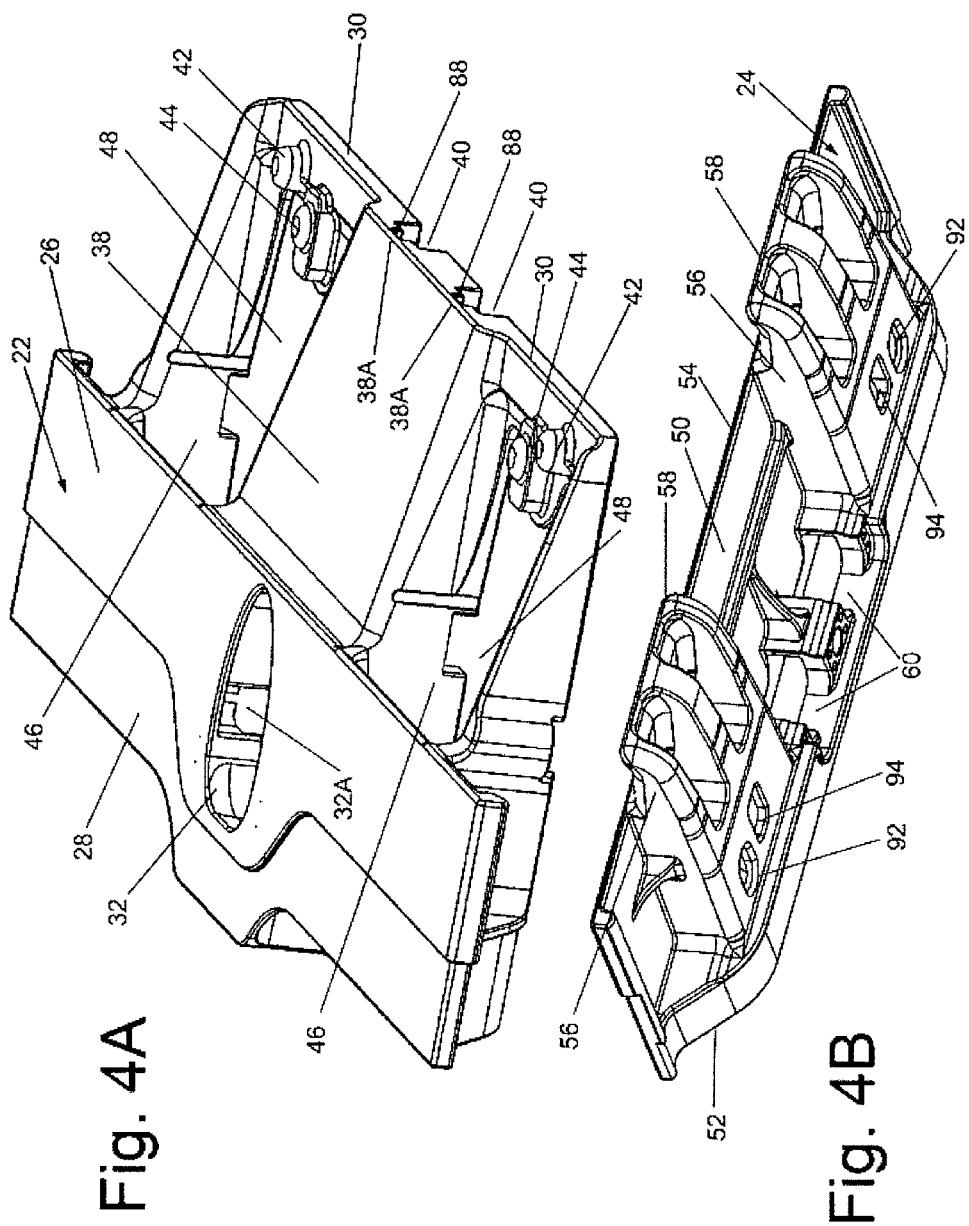

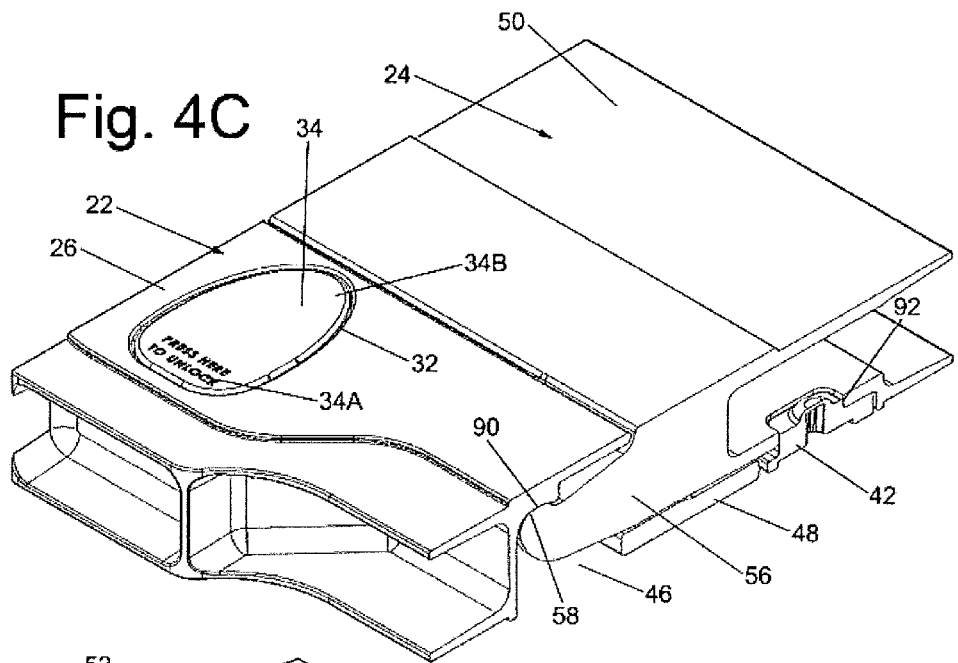
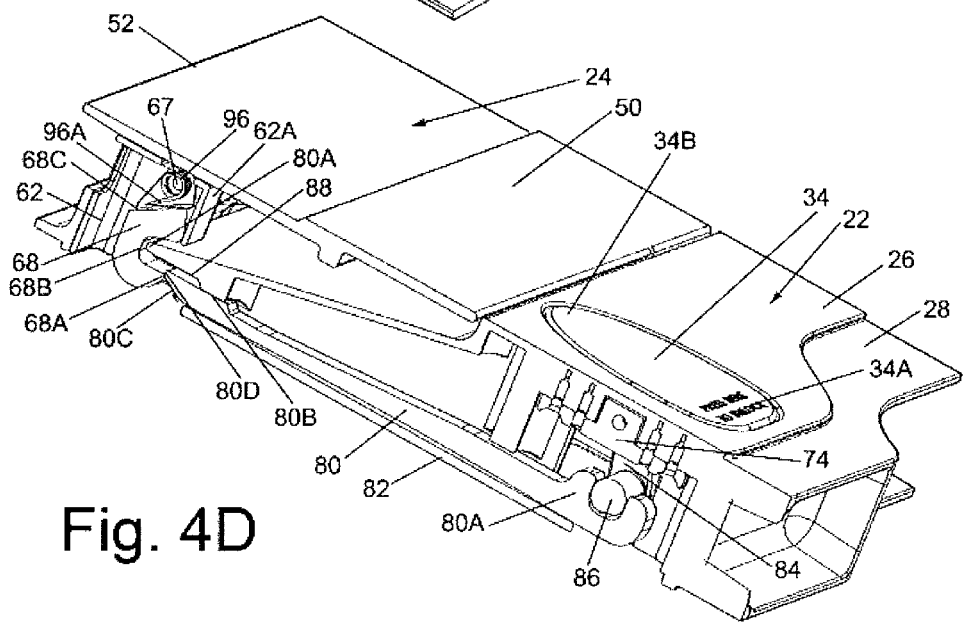

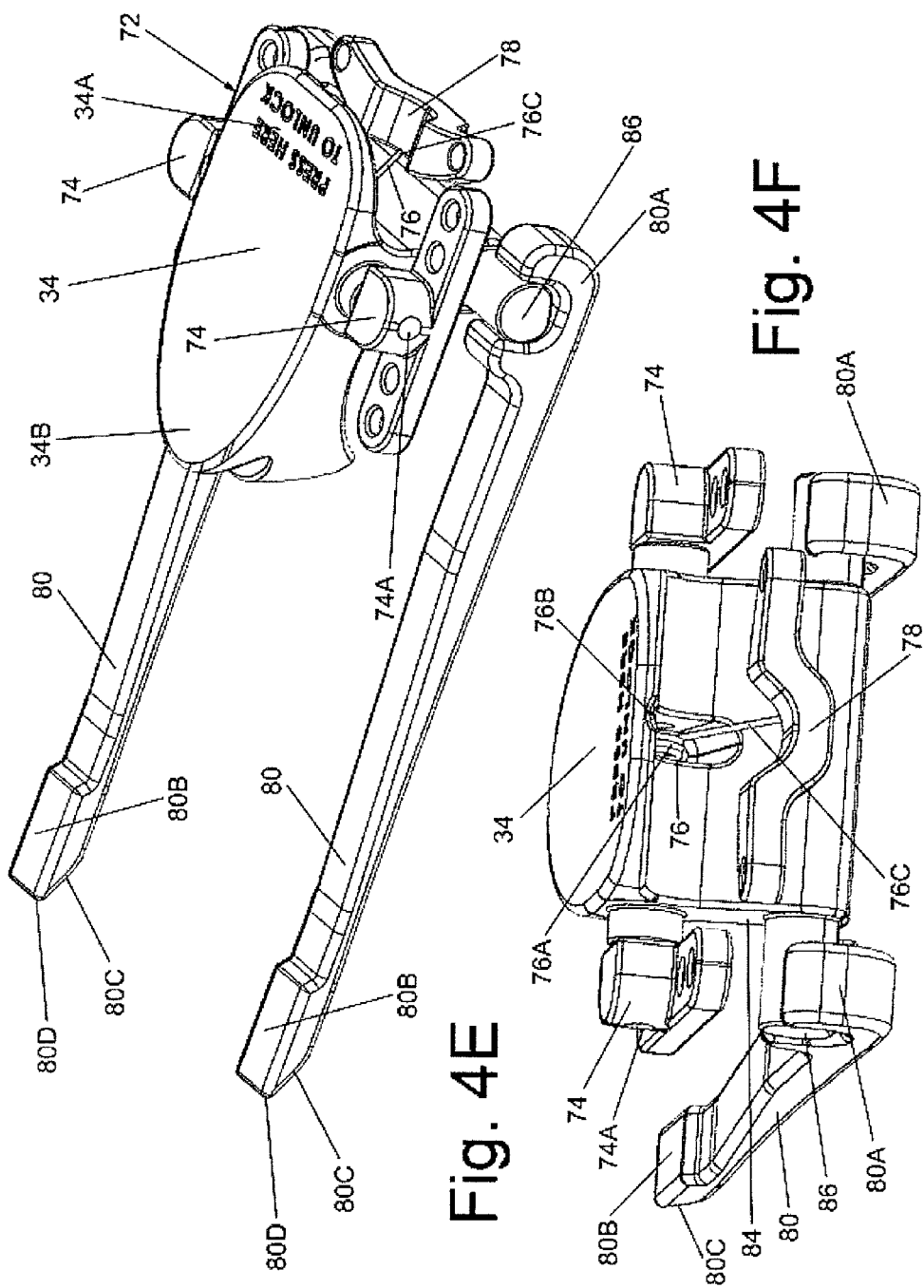

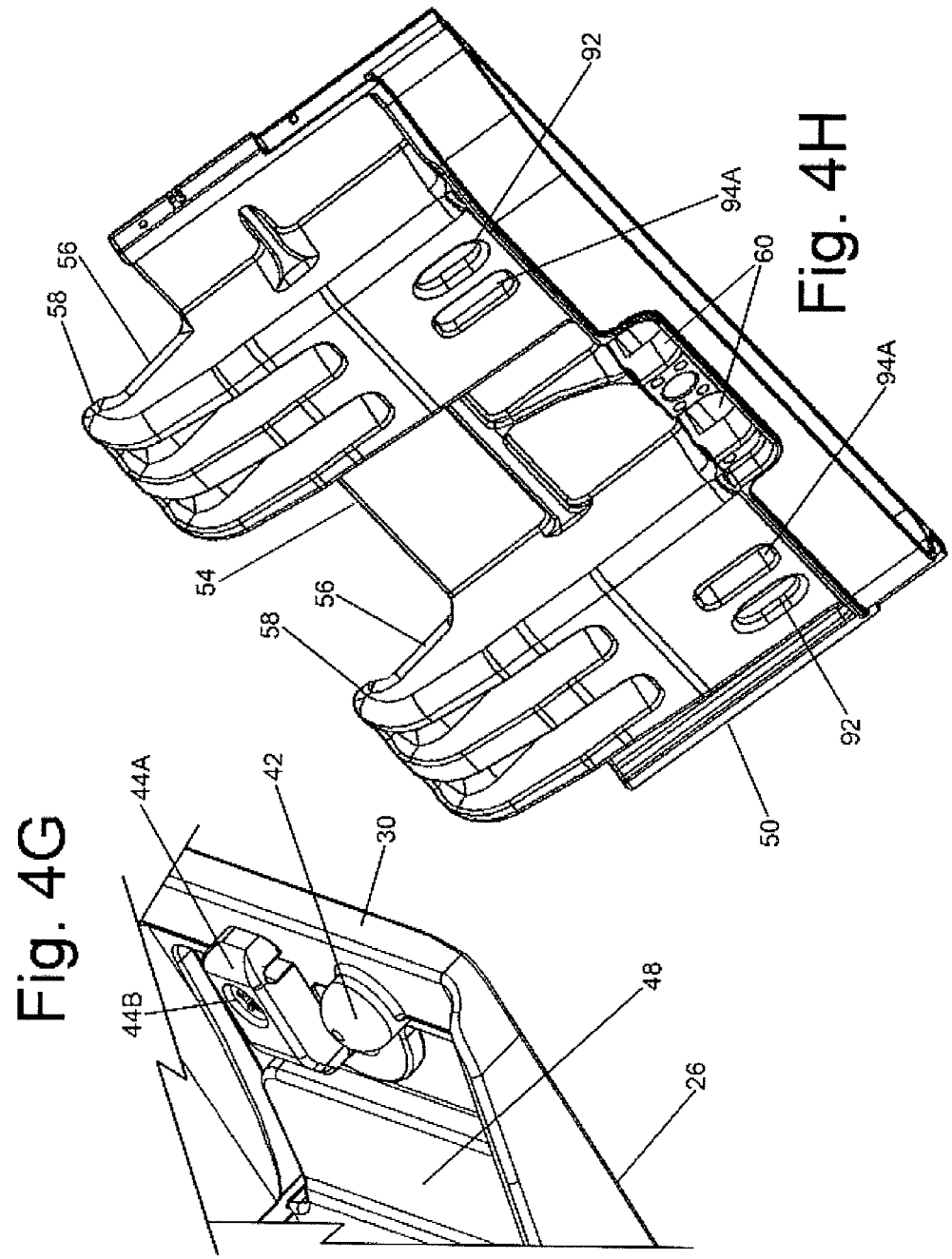

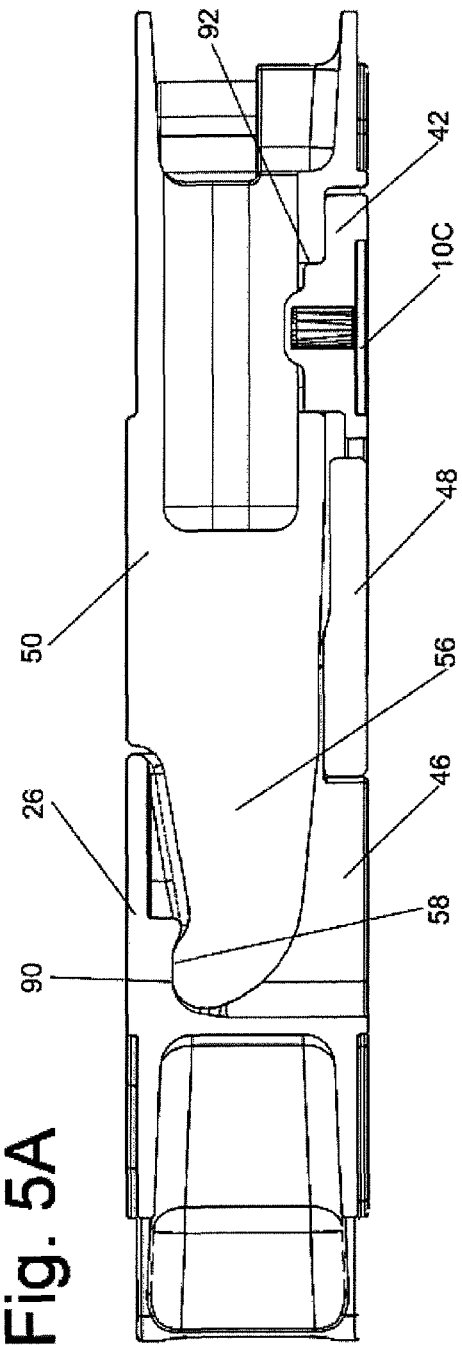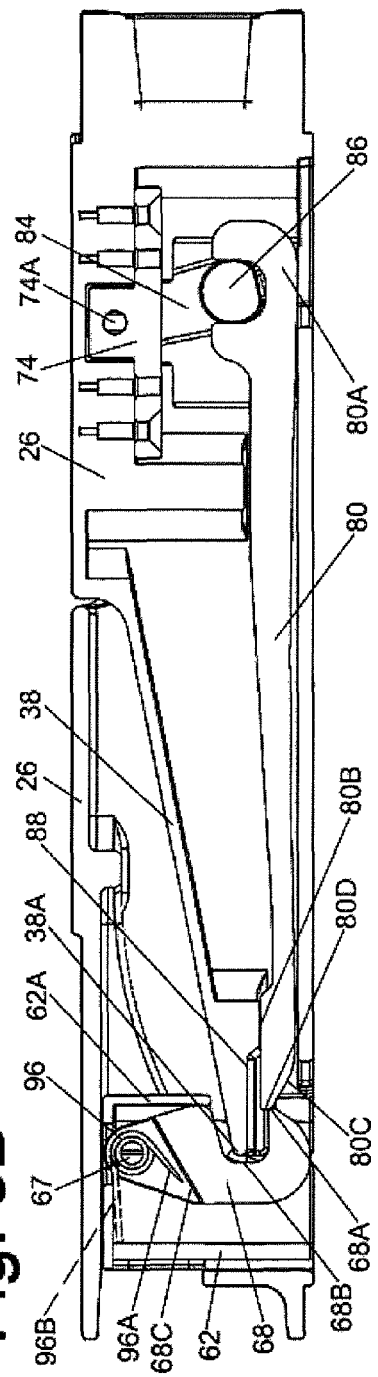
Fig. 5A
Fig. 5B

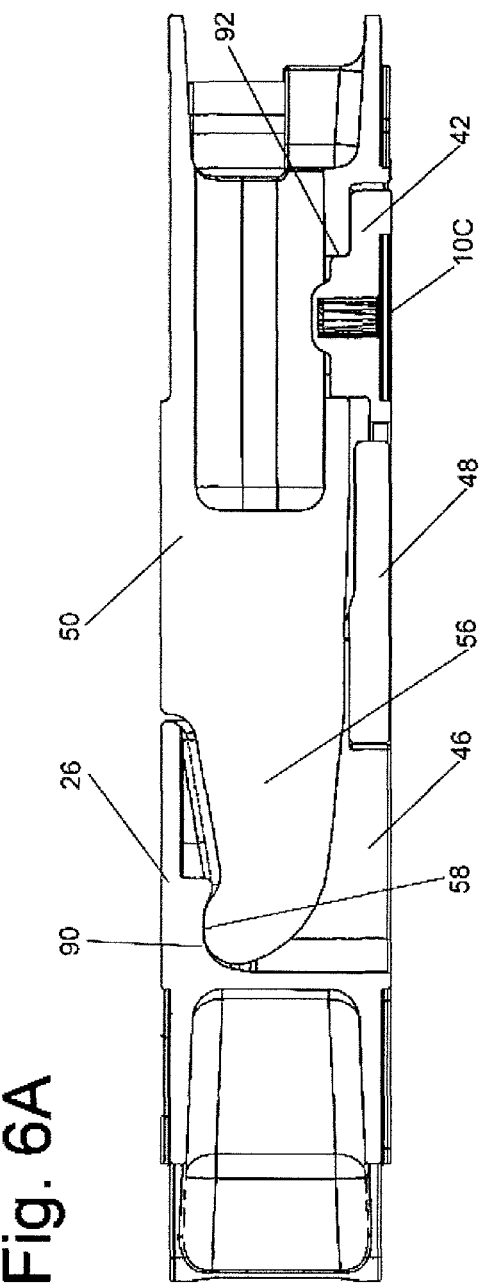
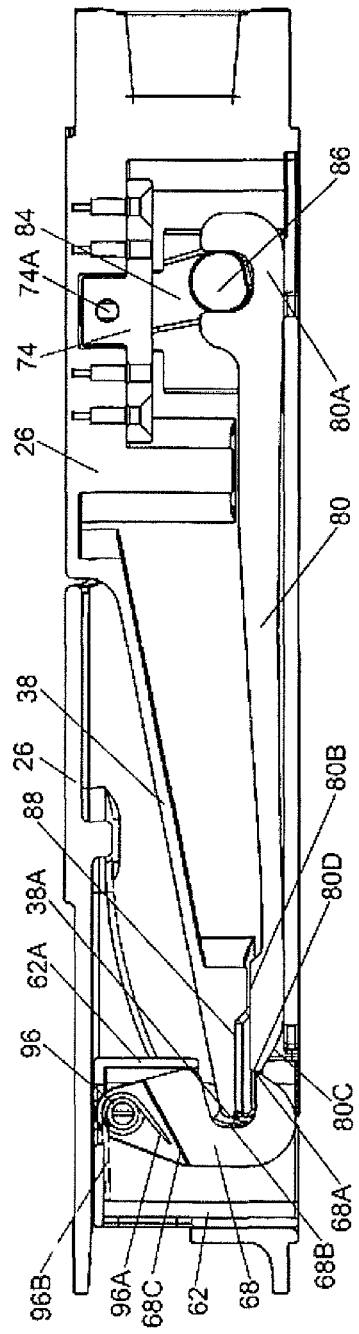
Fig. 6A
Fig. 6B

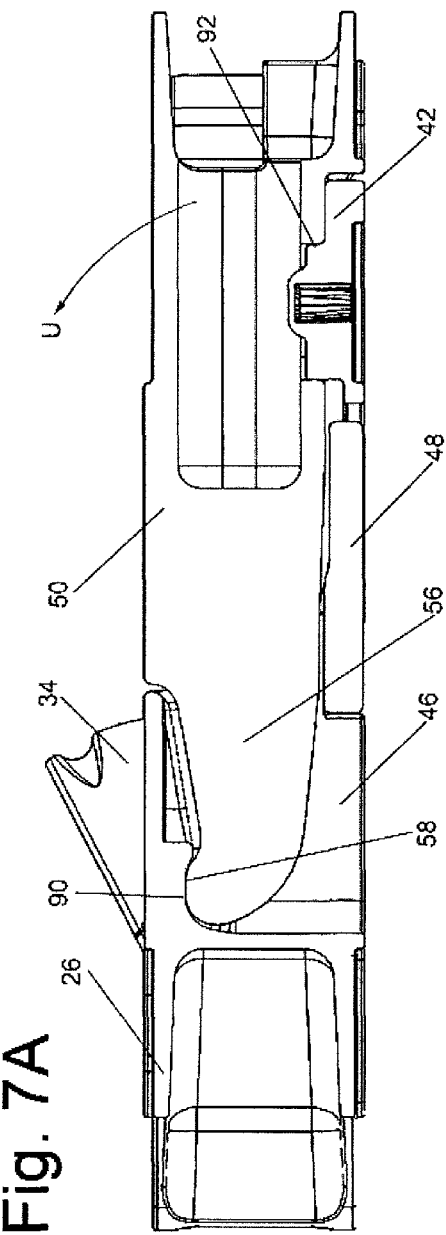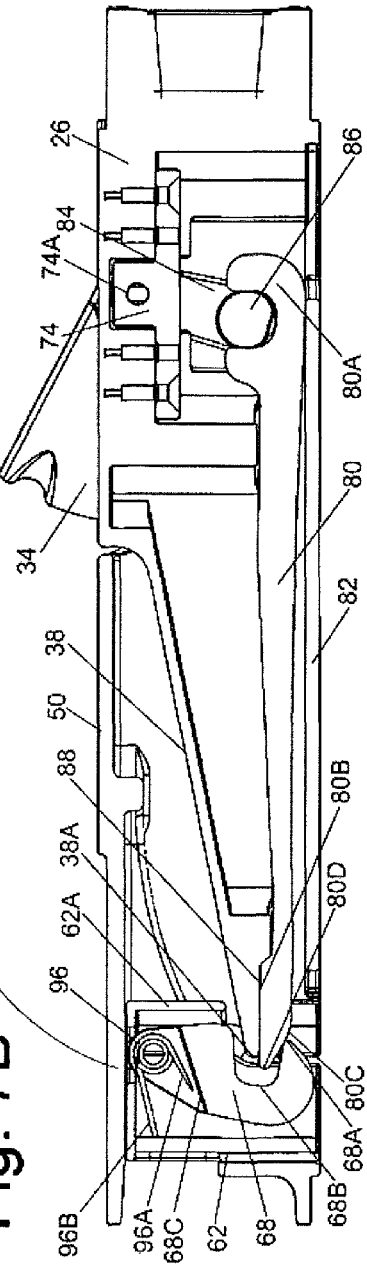

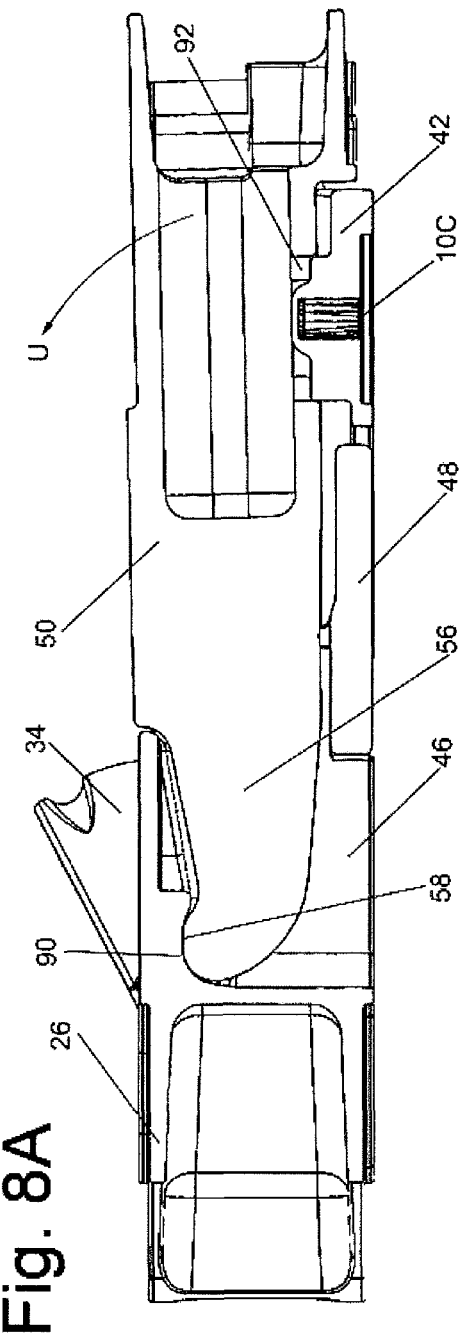
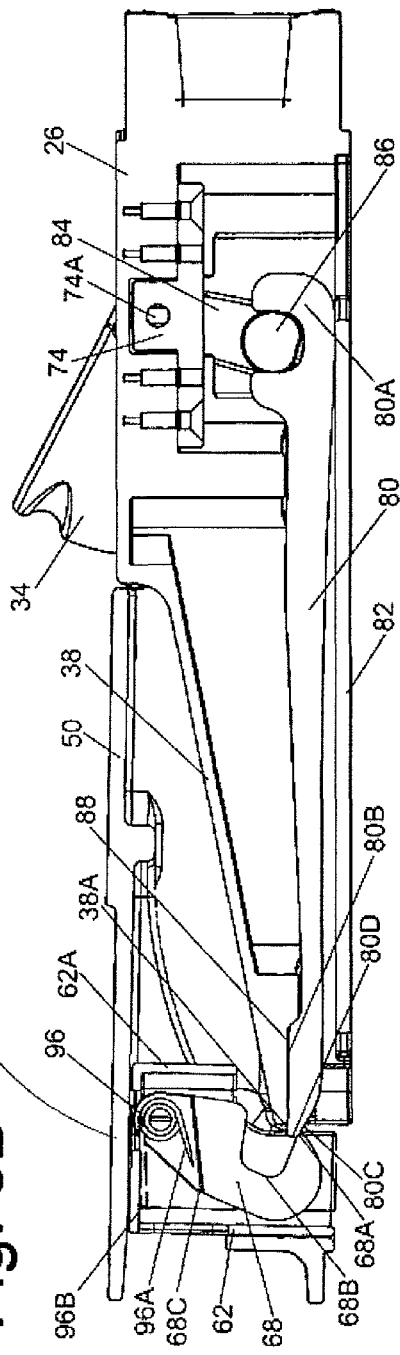
Fig. 8A
Fig. 8B

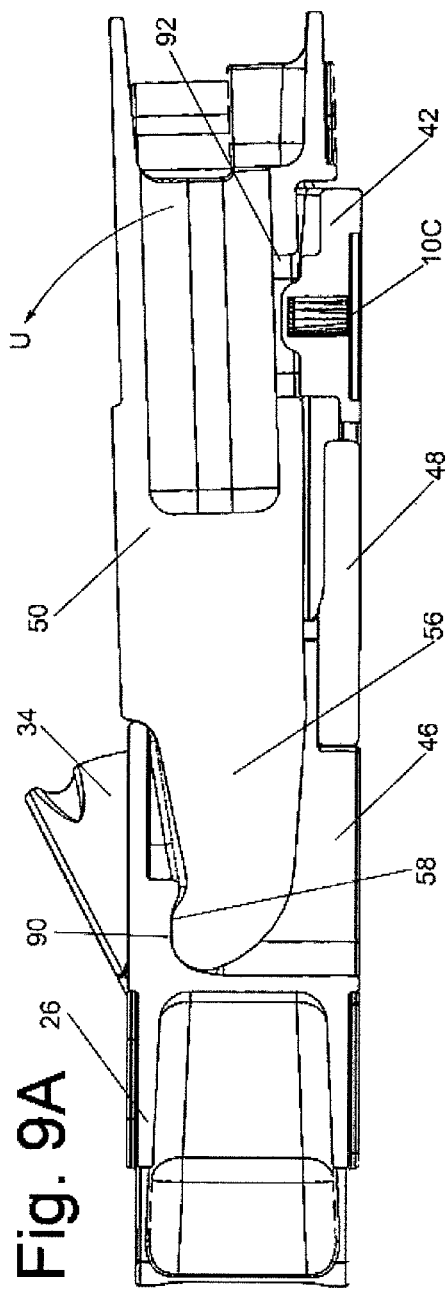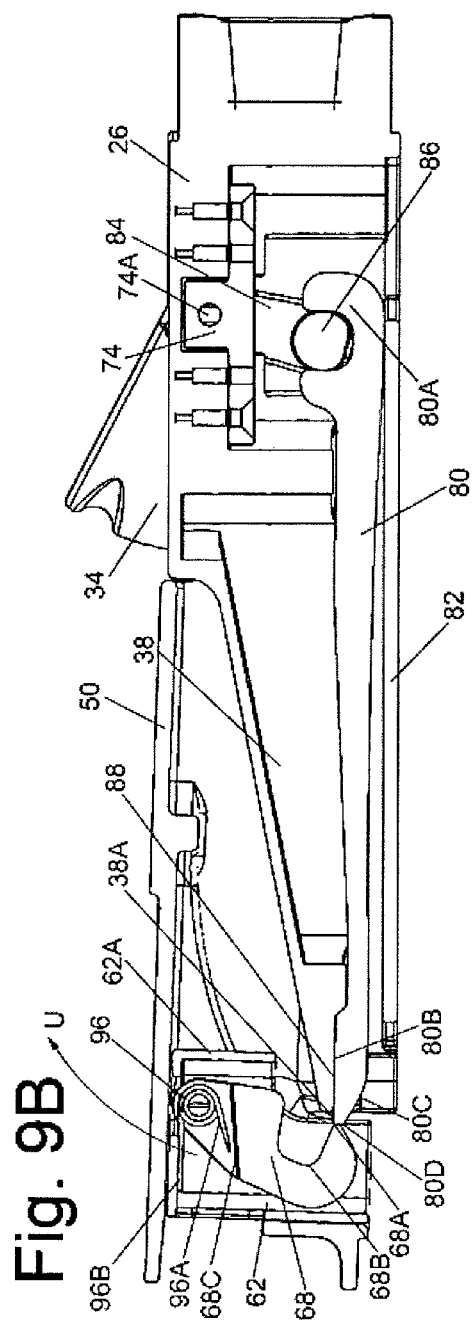

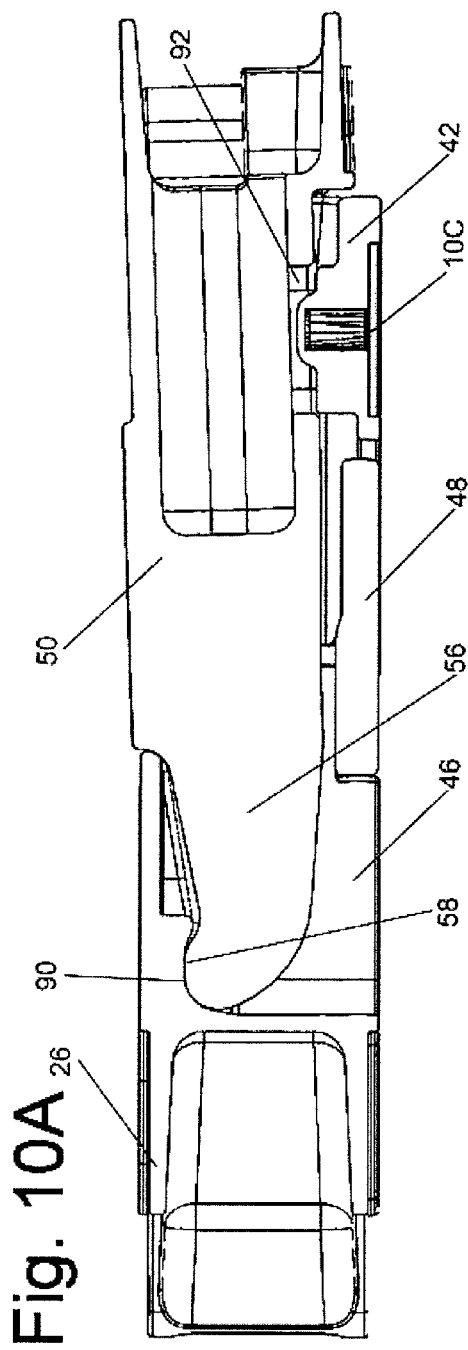
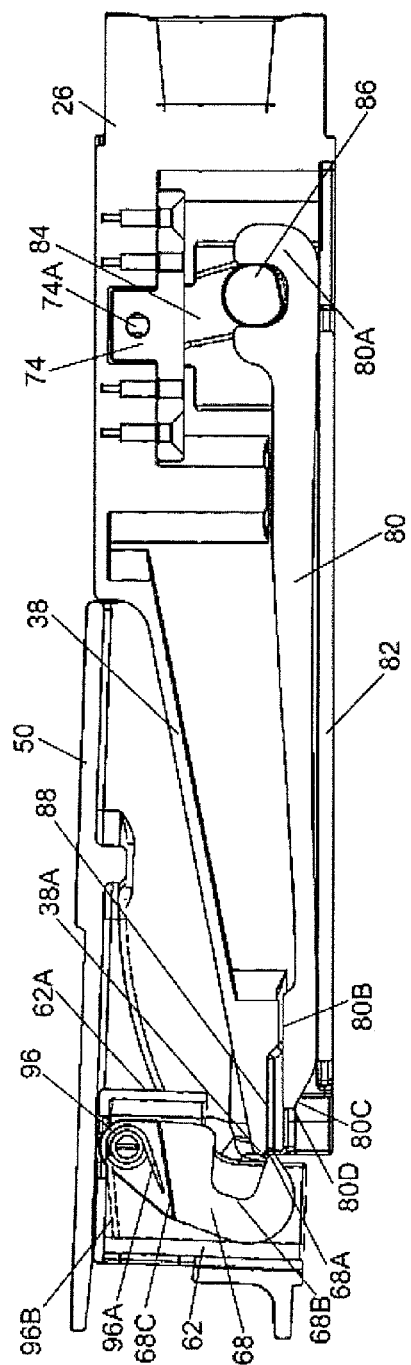
Fig. 10A
Fig. 10B

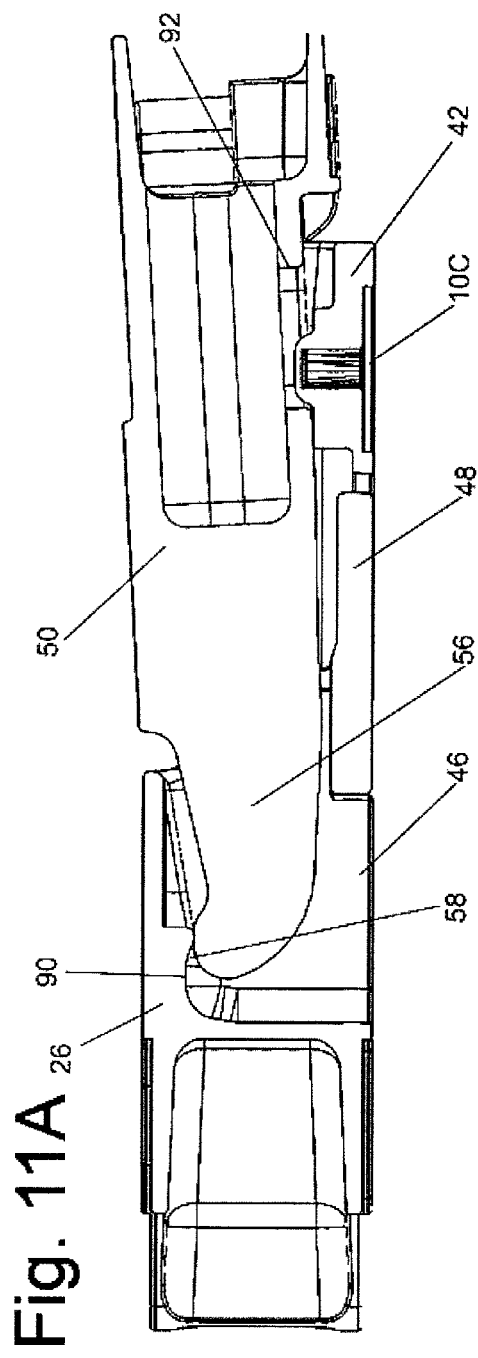
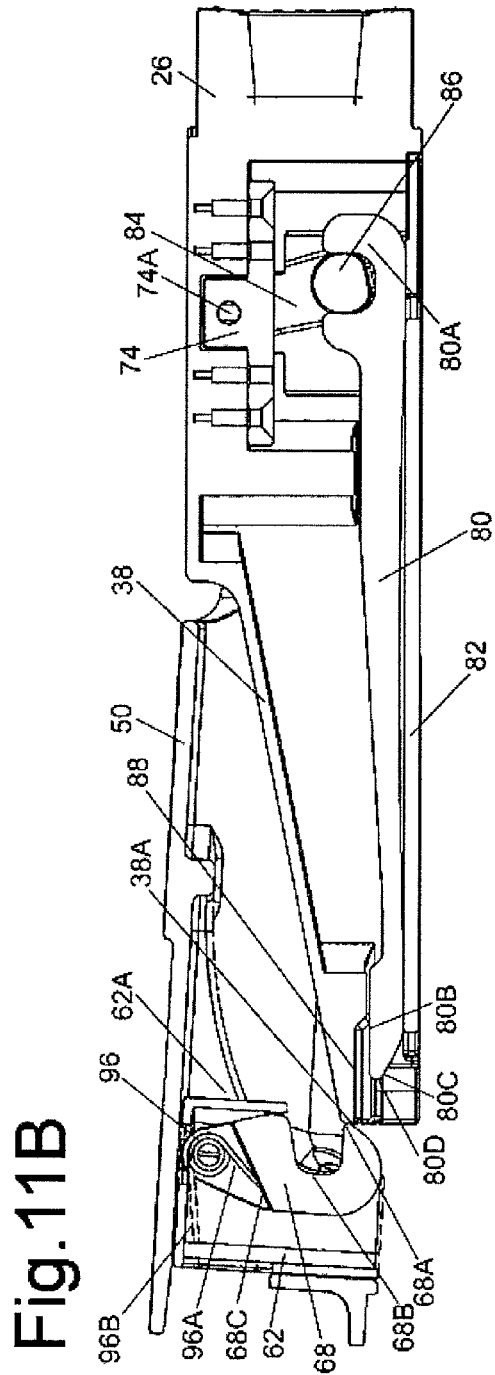
Fig. 11A
Fig. 11B

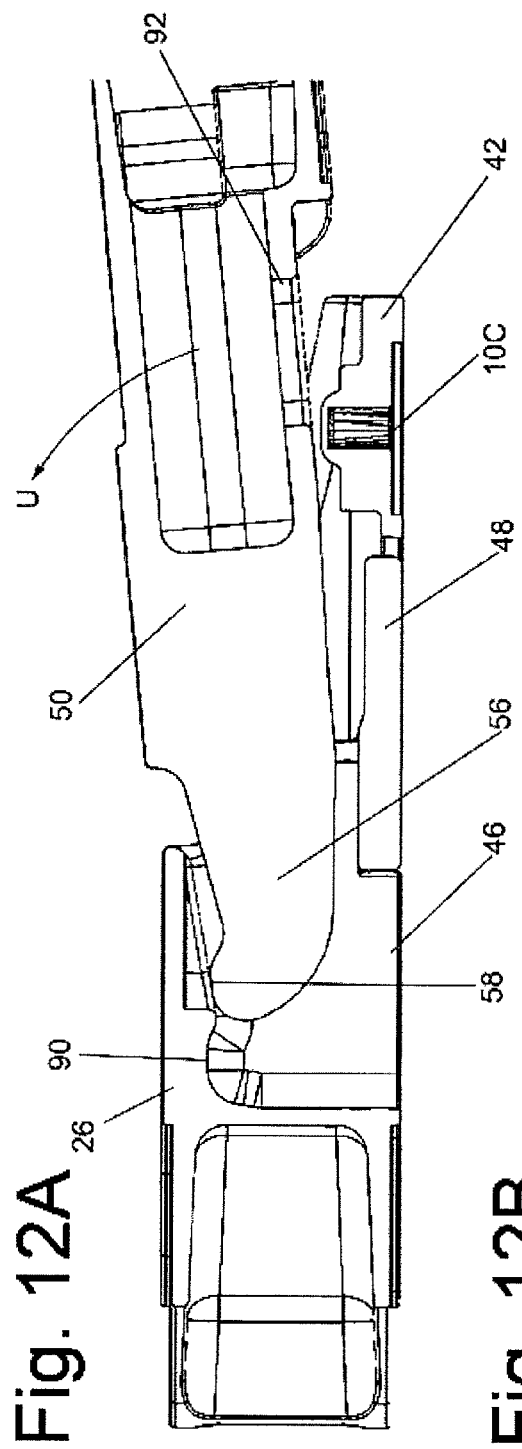
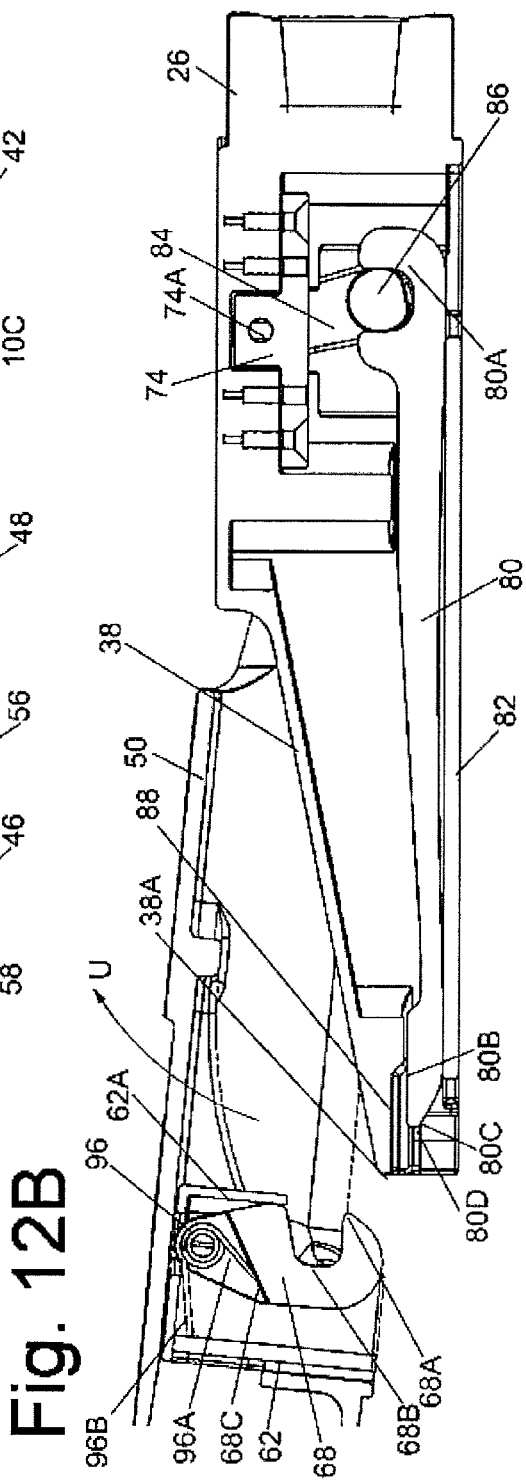
Fig. 12A
Fig. 12B

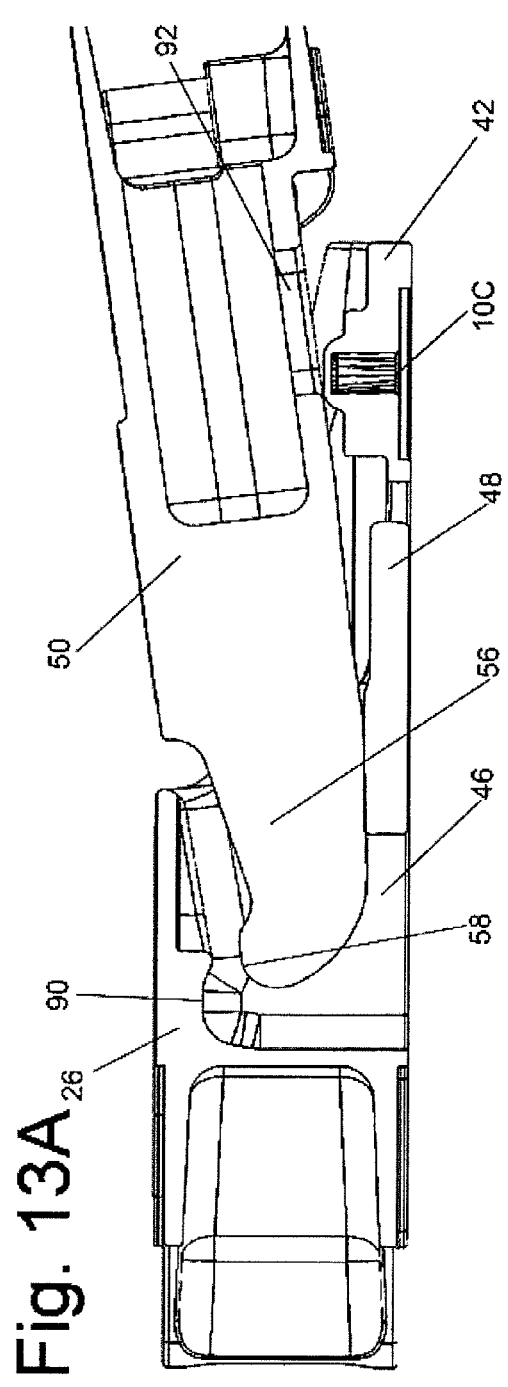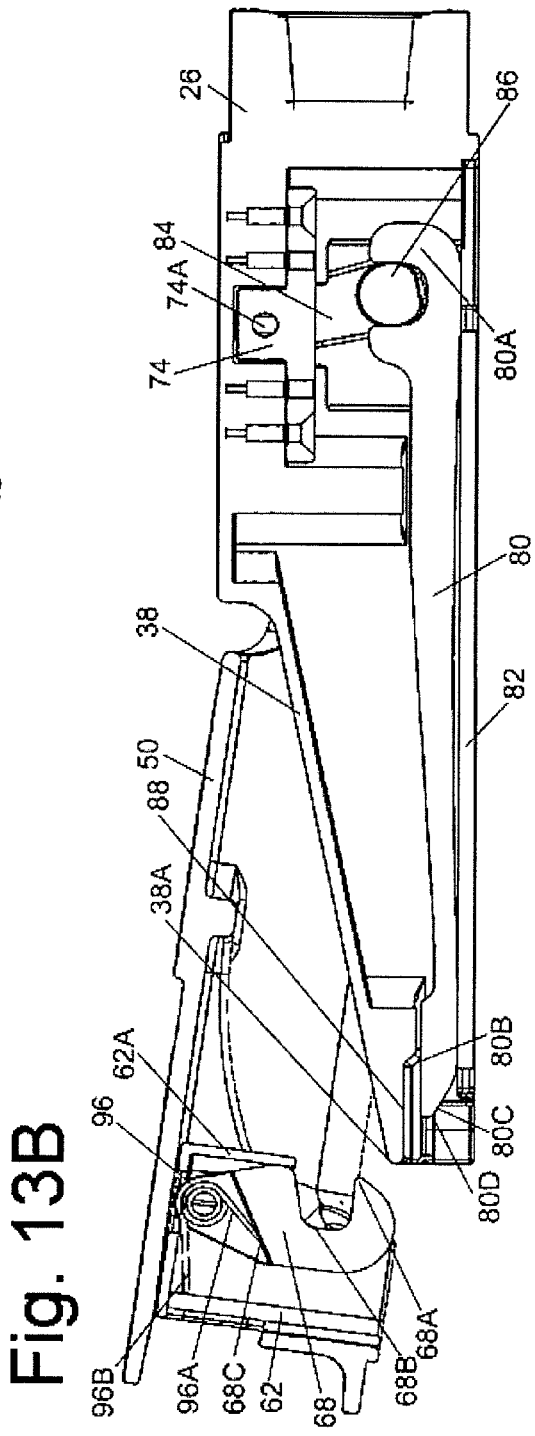

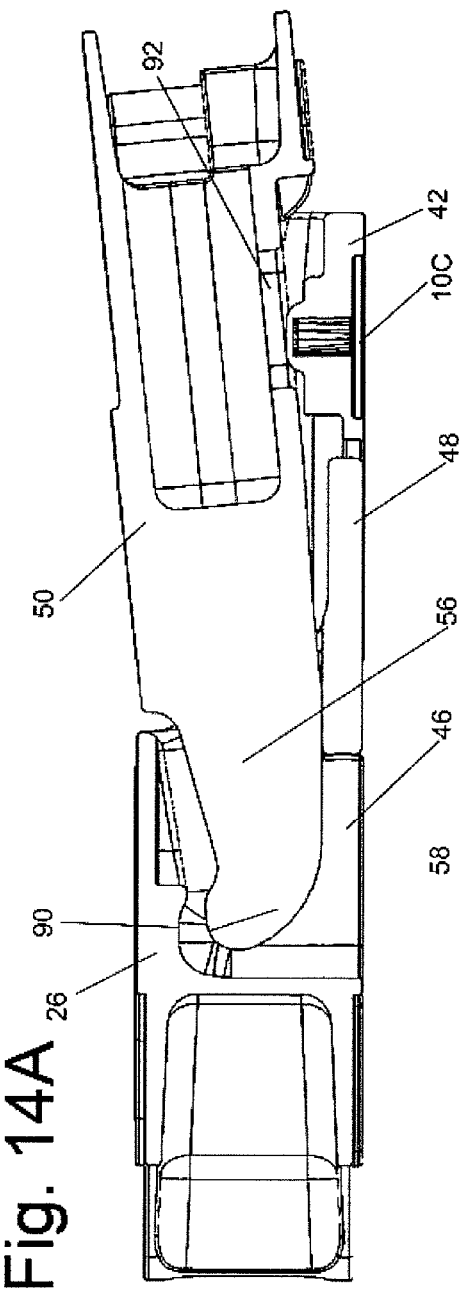
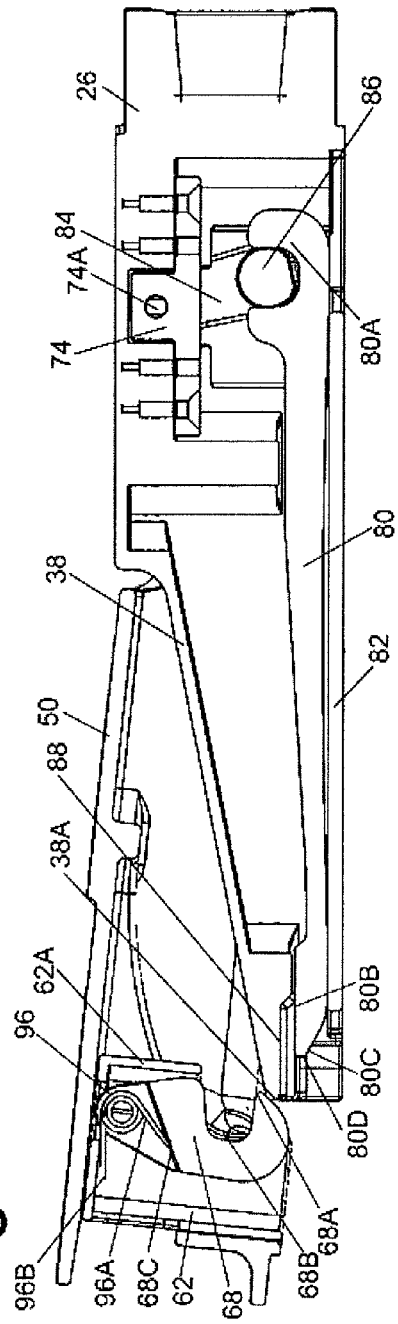
Fig. 14A
Fig. 14B

JOINT ASSEMBLY FOR CONNECTING A LONG EXTENSION PANEL TO A PATIENT SUPPORT PANEL OF A RADIATION THERAPY TABLE AND A TWO-PIECE PATIENT SUPPORT TABLE FORMED THEREBY

FIELD OF THE INVENTION

This invention relates generally to tables for supporting a patient for treatment and more particularly to patient supporting panels or couch-tops for radiation therapy having a releasably securable joint to enable an extension panel, e.g., a long, leg extension panel, to be readily connected to and disconnected therefrom.

BACKGROUND OF THE INVENTION

As is known medical tables are used with linear accelerators and simulators to provide a platform on which a patient can be disposed for radiation therapy. Such tables frequently include a patient support panel, sometimes referred to as a couch-top, constructed of carbon fibers or other suitable materials to provide both radiation friendly treatment and indexing capabilities. Moreover, such patient support panels frequently make use of additional treatment panels, such as head or leg extensions, connected to the patient support panel by a releasably securable joint to result in a two-piece radiation couch or table. Typically that joint is located either not far from the superior end of the patient support panel (where it can interfere with treatment and imaging) or may make use of support beams (which may interrupt and inhibit treatment delivery or clear imaging).

The following United States patents and printed publications relate to medical treatment tables with sections or extensions that may mounted thereon: U.S. Pat. No. 7,540,661 (Hornig); U.S. Pat. No. 7,076,821 (de Mooy); U.S. Pat. No. 6,941,599 (Zacharopoulos, et al.); U.S. Pat. No. 6,912,959 (Kolody, et al.); U.S. Pat. No. 6,557,195 (Dinkler); U.S. Pat. No. 6,199,233 (Kantrowitz, et al.); U.S. Pat. No. 5,675,851 (Feathers); U.S. Pat. No. 5,661,859 (Schaefer); US 2009/0308400 (Wilson, et al.); US 2007/0214570 (Coppens, et al.); WO 2009/029524 (Allen Medical Systems, Inc.); and WO 2005/004723 (Schaefer Mayfield USA, Inc.).

All references cited and/or identified herein are specifically incorporated by reference herein.

SUMMARY OF THE INVENTION

In accordance with one aspect of the invention a joint assembly is provided for releasably connecting an extension panel to a patient support panel (e.g., a patient support panel mounted on a pedestal adjacent a radiation therapy apparatus). The joint assembly enables the extension panel to be readily connected to and disconnected from the patient support panel. With the extension panel secured to the patient support panel by the joint assembly, a patient can be disposed on the extension panel for therapy.

Another aspect of this invention is the combination of the patient support panel, the joint assembly and the extension panel.

The joint assembly basically comprises a first body member and a second body member. One of the first and second body members is arranged to be secured to the patient support panel and the other of the first and second body members is arranged to be secured to the extension panel. The first body member comprises an actuator assembly (e.g., a spring-biased pivotable button and an associated extendable-retractable lever) and a frame. The frame includes a projection, a first locking member and an overhang having an undersurface with a recess therein. The second body member comprises a movable latch member and a frame. The frame includes at least one tab member and a second locking member.

The second body member with the extension secured thereto is arranged to be brought into engagement with first body member, whereupon a portion of the at least one tab member is releasably received within the recess of the first body member and with the first and second locking members engaging each other to lock the first and second body members together. This action prevents downward movement of the extension panel with respect to the patient support panel. The action of the movable latch member of the second body member engaging the projection of the first body member acts as a secondary lock which locks the first and second body members together and thereby prevents upward movement of the extension panel with respect to the patient support panel.

DESCRIPTION OF THE DRAWING

FIG. 1 is an isometric view of one exemplary embodiment of the combination of a patient support panel, an extension panel and a joint assembly, the joint assembly comprising two body members for releasably securing the extension panel to the patient support panel, all of those components being constructed in accordance with one aspect of this invention;

FIG. 2 is an enlarged exploded isometric view of a portion of the patient support panel, the extension panel and the two body members of the joint assembly shown in FIG. 1, with one portion of one body member removed;

FIG. 3 is an enlarged bottom plan view of the joint assembly and contiguous portions of the patient support panel and the extension panel shown in FIG. 1;

FIG. 4A is an enlarged isometric view of the frame of one body member making up the joint assembly, which body member is secured to the patient support panel of FIG. 1;

FIG. 4B is an enlarged isometric view of the frame of the other body member making up the joint assembly, the other body member being secured to the extension panel of FIG. 1;

FIG. 4C is an enlarged sectional isometric view of one the longitudinal section of the joint assembly of FIG. 1 showing its two body members in their fully locked state (called the "locked stage"), the longitudinal section being taken between section lines 4C and 4D of FIG. 1 and in the direction of the section line 4C;

FIG. 4D is a view similar to FIG. 4C but showing the longitudinal section of the joint assembly taken in the direction of section line 4D;

FIG. 4E is an enlarged exploded isometric view of a portion of the actuator subassembly forming a portion of the body member secured to the patient support panel;

FIG. 4F is another enlarged exploded isometric view of the portion of the actuator subassembly shown in FIG. 4E;

FIG. 4G is an enlarged isometric view of a portion of the frame shown in FIG. 4A making use of a pair of alternative bosses (only one of which is shown in FIG. 4H);

FIG. 4H is another isometric view of the frame shown in FIG. 4B, but making use of a pair of alternative recesses for receipt of the alternative bosses shown in FIG. 4H;

FIGS. 5A and 5B are sectional views of the sides of the fully locked joint assembly section shown in FIGS. 4A and 4B, respectively;

FIGS. 6A and 6B are sectional views similar to FIGS. 5A and 5B, respectively, showing the two body members of the joint assembly in their locked state with an upward force applied to the extension (called the "locked-uploaded stage"), whereupon the locking assembly resists disconnection;

FIGS. 7A and 7B are side elevation views similar to FIGS. 5A and 5B, respectively, but showing the two body members of the joint assembly at the state at which release (the unlocking of the two bodies) is initiated (called "release stage 1") by the manual actuation of a pivotable button forming a portion of an actuation sub-assembly of the joint assembly;

FIGS. 8A and 8B are side elevation views similar to FIGS. 7A and 7B, respectively, but showing the two body members of the joint assembly in their next sequentially occurring state (called "release stage 2") wherein the body members and the panels connected to each are in the process of being undocked or separated from each other;

FIGS. 9A and 9B are side elevation views similar to FIGS. 8A and 8B, respectively, but showing the two body members of the joint assembly in their next sequentially occurring state (called "release stage 3") wherein the body members and the panels connected to each are being undocked;

FIGS. 10A and 10B are side elevation views similar to FIGS. 9A and 9B, respectively, but showing the two body members of the joint assembly in their next sequentially occurring undocking state (called "release stage 4");

FIGS. 11A and 11B are side elevation views similar to FIGS. 10A and 10B, respectively, but showing the two body members of the joint assembly in their next sequentially occurring undocking state (called "release stage 5");

FIGS. 12A and 12B are side elevation views similar to FIGS. 11A and 11B, respectively, but showing the two body members of the joint assembly in the final state of their undocking (called "release stage 6"), whereupon the extension panel is removed from the patient support panel;

FIGS. 13A and 13B are side elevation views similar to FIGS. 5A and 5B, respectively, but showing the two body members of the joint assembly when in the state at which they are being juxtaposed so that they may be docked and subsequently locked together (called "insertion stage 1"); and FIGS. 14A and 14B are side elevation views similar to FIGS. 7A and 7B, respectively, but showing the two body members of the joint assembly in their next sequentially occurring state (called "insertion stage 2") to dock them together so that they can be brought into the fully locked state shown in FIGS. 4A and 4B and FIGS. 5A and 5B.

DETAILED DESCRIPTION OF THE PREFERRED EMBODIMENT

Referring now to the various figures of the drawing wherein like reference characters refer to like parts, there is shown in FIG. 1 a patient support panel 10, an extension panel 12 and a joint assembly 20 constructed in accordance with one exemplary embodiment of this invention. The joint assembly is arranged for releasably securing the panels 10 and 12 together. The patient support panel 10 is a generally planar member having a top surface 10A. The panel 10 is arranged to be secured onto the top of a pedestal or base (shown by the phantom lines 14) located adjacent radiation therapy apparatus, e.g., a LINAC (not shown). The patient support panel is of sufficient size to support at least a portion of an adult patient in a prone position thereon. In the interests of non-interference with the radiation produced by the radiation equipment, the patient support panel 10 is preferably formed of any suitable radiation transparent material, e.g., a carbon composite. Moreover, it may include features, e.g., side rails, (not shown) for mounting radiation therapy assisting components, e.g., positioning masks, positioning cushions, fiducial marker frames, etc. (not shown) thereon. The extension panel 12 also comprises a generally planar member having a top surface 12A and is preferably formed of the same material as the patient support panel. If desired, the extension panel may include side rails or other features to mount radiation therapy assisting components thereon.

The joint assembly 20 of this invention is amenable to location near the superior end of the pedestal on which the patient support panel 10 is mounted. In fact, that is the preferred (although not mandatory) location for the joint assembly. The extension panel is a relatively long member, e.g., 53 inches (134.6 cm). Thus, with extension panel 12 secured to the patient support panel 10 by the joint assembly 20, one is able to provide a two-piece patient support table including a long portion provided by the extension panel which is of consistent construction and density to the patient support panel. This greatly expands the effective area available for imaging and treatment without varying or unacceptable interference. Thus, most if not all of the patient can be disposed on the extension panel. To that end, the joint assembly 20 and the extension panel 12 are formed of materials and are constructed to be sufficiently strong to support any adult on the extension panel, even though it will be cantilevered out from the pedestal 14 by a substantial distance as shown in FIG. 1. The patient support panel is secured to the top of the pedestal 14 by plural threaded fasteners extending into threaded holes 10C in the underside of the patient support panel 10 as best seen in FIG. 3.

The construction and operation joint assembly 20 will be described in considerable detail later. Suffice it for now to state that the joint assembly includes one body member 22 fixedly secured to the patient support panel 10 and another body member 24 fixedly secured to the extension panel 12. The body member 24 with the extension panel secured to it is arranged to be docked to and releasably secured to the body member 22 (which is secured to the patient support panel and mounted on the pedestal). When those two body members and their associated panels are docked and releasably secured the joint assembly self aligns, self levels, is immediately stable and locks automatically by the weight and downward pressure on the extension panel 12. The joint assembly 20 also includes an automatic fail-safe secondary lock (to be described later) that resists release of the joint assembly if upward forces are applied to the extension panel 12. Disengaging the secondary lock requires and results in no displacement of the body members 22 and 24, thereby facilitating use of the patient support structure and eliminating the need for the mechanism to overcome large cantilever forces to function. Upon separation of the two body members the secondary lock of the joint assembly resets itself automatically. In so doing it is ready to automatically lock the extension panel 12 back to the patient support panel 10 when the extension panel with its associated body member 24 is again docked to the body member 22. If the two body members 22 and 24 of the joint assembly are not separated after disengaging the secondary lock, the secondary lock can be readily re-engaged manually.

As will also be described in detail later, the joint assembly includes an actuator subassembly including a manually operative member, e.g., a pivotable button, whose operational position functionally and visually indicates if the joint assembly is locked or unlocked. Furthermore the secondary lock is constructed so that it will not remain in the unlocked position when the two body members of the joint assembly are not docked together.

Turning now to FIG. 1, it can be seen that the body member 22 of the joint assembly is located and secured a the top end 10B of the patient support panel, while the body 24 of the joint assembly is located and secured to the bottom end 12B of the extension panel 12. This arrangement results in a lightweight, robust, two part radiation therapy treatment patient support that employs a unique connecting joint for removably attaching extension panels of various lengths and configurations to a patient support panel fixedly mounted on a pedestal adjacent a radiation therapy apparatus. The connection of the two panels provided by the joint assembly 20 is located well away from the treatment/imaging areas, thus providing advantages to both by eliminating the high attenuation, artifacts, and density variations one normally encounters if the joint is in the treatment field. Moreover, as will be seen later, the joint assembly further enhances these advantages by eliminating the addition of support beams commonly found in prior art long extension systems. Instead the joint assembly of this invention makes use of a unique construction and arrangement that nicely manages the increased demands both structurally and functionally inherent in a cantilevered configuration.

Referring now to FIGS. 2 and 4D, it can be seen that the body member 22 basically comprises a unitary frame 26. The frame serves to support the various other components making up the body member 22. In accordance with a preferred embodiment of this invention the frame 26 is formed of a strong and rugged material, e.g., aluminum, but other suitable materials can be used as well. The frame includes a proximal portion 28 and a distal portion 30. The proximal portion 28 is arranged to be received within and permanently secured to a correspondingly shaped cavity (not shown) in the end 10B of the patient support panel 10 to thereby fixedly secure the body member 22 to that panel. An opening 32 and associated cavity is provided in the frame 26 for receipt of an actuator subassembly which effects the operation of the heretofore mentioned secondary lock. The details of the actuator subassembly will be described later. Suffice it for not to state that it includes a spring biased button 34 which is located within the opening 32 and associated recess in the frame 26.

The distal end of the frame 26 includes a pair of downwardly tapering sidewalls 36 and a downwardly sloping wide central wall 38. The central wall forms a distal projection arranged to be engaged by the secondary lock, as will be described later. The underside of the central wall or projection 38 includes a pair of longitudinally extending recesses 40 for receipt of respective ones of levers making up the actuator subassembly. The upper portion of each recess 40 is of narrower width than the bottom portion of each recess. It is within the upper portion of each recess that a respective lever forming a portion of a secondary lock actuator subassembly is located. The front end of the projection 38 at the top portion of the recesses 40 is designated by the reference number 38A. It is the portions 38A which are arranged to be engaged and trapped by a latch member (to be described later) forming a portion of the secondary lock. The front of the projection 38 is connected to the front edge of each of the sidewalls 36 by the distal portion 30 which forms a pair of bridging sections. Two pair of bosses 42 and 44 projects upward from the bridging sections. The pair of bosses 44 are located on respective extensions of the two bridging section so that they are located toward the proximal end of the frame 26.

The respective spaces between the sidewalls 36 and the central wall or projection 38 form a pair of cavities 46 in the frame 26 for receipt of tabs (to be described shortly) forming a portion of the frame of the body member 24. A pair of guide plates 48 is secured to the undersurface of the frame 26 within the respective cavities 46 to form the bottom of each of the cavities 46.

Turning now to FIGS. 2 and 4B, it can be seen that the body member 24 basically comprises a unitary frame 50. The frame serves to support the various other components making up the body member 24. In accordance with a preferred embodiment of this invention the frame 50 is formed of a strong and rugged material like that of frame 26, but other suitable materials can be used as well. The frame includes a proximal portion 52 and a distal portion 54. The proximal portion 52 is arranged to be received within and permanently secured to a correspondingly shaped cavity (not shown) in the end 12B of the extension panel 12 to thereby fixedly secure the body member 24 to that panel. The distal end portion 54 of the frame 50 includes a pair of projecting tabs 56, each including a convex upturned free end surface 58. The tabs 56 are arranged to be received within respective ones of the recesses 46 in the frame 26 when the two body members 22 and 24 are docked and locked together, as will be described later. The underside of the proximal end of the frame 50 includes a recess 60 (FIG. 4H) for receipt of a pair of retainer boxes 62 (FIGS. 3 and 4D). The retainer boxes 62 are mounted to the recess 60 via bolts extending into threaded holes in the recess.

The secondary lock will be described in further detail later. Suffice it to say that it basically comprises a pair of spring biased latches 68, each pivotably mounted within a respective retainer box 62 via a pivot pin 67 (FIGS. 4D and 5B) extending through aligned holes in the opposed sidewalls of the retainer box 62. The latches are biased by respective springs (to be described later) so that each pivots to a closed or extended position at which it engages the a respective portion 38A at the free end of the projection 38 of the frame 26 to trap it when the two body members 22 and 24 are in the locked position like shown in FIGS. 4D and 5B. Each of the latches 68 is arranged to be pivoted from the closed or extended position against the bias of its associated spring by the engagement of the free end of a respective lever forming a portion of the actuator subassembly.

Turning now to FIGS. 4E and 4F, the details of the actuator subassembly 70 will now be described. To that end, the actuator subassembly basically comprises the heretofore identified pivotable button 34, a pair of mounting brackets 74, a spring 76, a stop member 78, a pair of levers 80 and a pair of retainer plates 82 (FIGS. 3 and 4D). The button 34 includes a flat top surface having a first end 34A on which indicia "PRESS HERE TO UNLOCK" is provided and a second end 34B located opposite end 34A. The brackets 74 are mounted within respective recesses 32A (FIG. 4A) the frame 26 of the body member 22 via screws (not shown). The stop member 78 is mounted within a hollow portion of the frame 26 via respective mounting screws (not shown). A pivot rod 74A is journalled in the brackets 74 and extends through a transverse passageway in the button 34. It is about this rod that the button 34 is arranged to pivot.

As best seen in FIG. 4F the spring 76 includes a helical central section 76A through which the pivot rod 74A extends and a pair of linear ends 76B and 76C. The linear end 76C engages and is trapped in the V-shaped center portion of the stop member 78, while the linear end 76B engages and is trapped in a curved recess in the portion 34A of the button 34 underlying the indicia. The button 34 is biased by the spring 76 so that it tends to assume the position shown in the locked state of FIGS. 4C and 4D, whereupon its upper surface is flush with the upper surface of the frame 26 in which it is located. The stop member 78 not only serves to provide a fixed surface against which the linear end 76c of the spring engages, but also serves as a physical stop for the end portion of the button on which the indicia appears when that button is pushed to effect the release of the secondary lock.

The underside of the button 34 includes a downwardly extending link 84 (FIG. 4F) from which a pair of rod-like members 86 project outwardly along a common axis. Each of the rod-like members is arranged to be coupled to an end of a respective lever 80. To that end, each lever 80 includes a yoke 80A at one end in which a respective rod-like member 86 of the link 84 is received. Each lever 80 is an elongated member having a free end located opposite the yoke 80A. The free end of each lever 80 will be described soon. Suffice it for now to state that it is arranged to be disposed within the upper portion of an associated recess 40 in the frame 26. The section line 4C of FIG. 1 is taken through the centerline of the recess 40.

As best seen in FIG. 4E, the free end of each lever 80 includes an upwardly projecting flat mesa 80B, a tapering undersurface 80C and a free end surface 80D. The mesa 80B is arranged to be received within a correspondingly shaped 88 notch (FIGS. 4D, 5B, 7B, 8B, and 9B) at the entry to the upper portion of the recess 40 of the frame 26 of the body member 22. A respective retainer plate 82 is secured to the frame 26 by respective screws (not shown) so that it is located immediately below the lever 80 as shown in FIGS. 4D and 5B and thus serves to hold the lever in place.

As mentioned earlier the tabs 56 of the body member 24 are arranged to be received within the cavities 46 of the body member 22 when the two body members are docked together. Once they are docked the extension panel with the attached body member 24 can be oriented and moved so that its free end surface 58 is received within a correspondingly shaped recess 90 (FIGS. 4C and 5A) located on the undersurface of an overhanging portion of the frame 26 to lock the two body members and their associated panels together. Thus, the curved free end 58 of each tab and the corresponding curved recess 90 in which it is located serves as the primary lock for the joint assembly. The primary lock also includes two other components. In particular, the bosses 42 and 44 of the frame member 26 and corresponding recesses or apertures 92 and 94 (FIG. 4B) in the frame 50, serve as the other primary lock components. As will be described later the bosses 42 and 44 are arranged to be disposed within the apertures 92 and 94, respectively, when the two body members are locked together. These engaging bosses and apertures, coupled with the engaging tab surfaces 58 and recesses 90 prevent longitudinal and lateral displacement of the two body members with respect to each other. The secondary lock serves to prevent disengagement of the primary locking arrangement if an upward force is applied to the extension once it is in its locked state.

Turning now to FIGS. 4D, 5B and 7B, the details of the two latches 68 forming the secondary lock will now be described. As mentioned earlier the latches are disposed in respective retainer boxes 62. Each box includes a front wall 62A, a pair of opposed sidewalls (not shown) and a rear wall (not shown). Each latch is a pivotable hook-like member having a lower portion with a free end 68A and a recess or mouth 68B located immediately adjacent the free end 68A. The thickness of the latch is greater than the width of the upper portion of the recess 40 in which the free end of the lever is received, but is just slightly less than the width of the lower portion of the recess 40 so that it may fit within the lower portion of the recess 40 but not within the upper portion of the recess. The upper end of the latch 68 includes an aperture through which a pivot shaft 67 extends. Each pivot shaft extends through aligned openings in the opposed sidewalls of the associated retainer box, whereupon the associated latch is enabled to pivot about the pivot axis within the box. A pair of springs 96, similar to spring 76, is coupled to respective ones of the latches 68, with the pivot shaft 67 extending through the helical portion of the spring and with one linear portion 96A (FIG. 5B) of the spring engaging the bottom surface of a yoke 68C in the top portion of the latch 68 and the other linear portion 96B of the spring engaging the top surface of the associated retainer box. Thus, each latch 68 is biased to pivot outward (e.g., in the counterclockwise direction as shown in FIGS. 4D and 5B) about its pivot axis. The front wall 62A of each retainer box serves as a stop to prevent the associated spring from pivoting the associated latch beyond the orientation shown in FIGS. 4D and 5B, wherein both latches are in the position to trap the free end portions 38A of the body member 22.

Referring now to FIGS. 5A-11B, the operation of the joint assembly 20 to effect the disconnection (i.e., unlocking and undocking) of the extension panel 12 from the patient support panel 10 will now be described, it being assumed that the two panels had been previously docked and locked together. The state where they are locked together is shown in FIGS. 5A and 5B. In that state the free end 58 of each of the tabs 56 of the frame 50 of the body member 24 are disposed within respective ones of the recesses 90 in the undersurface of the frame 26 of the body member 22. In addition the bosses 42 and 44 of the frame 26 are received within their respective recesses or apertures 92 and 94 of the frame 50. Those engagements effect the primary locking of the body member 22 and 24 together, thereby rendering the extension panel 12 resistant to downward pivoting with respect to the patient support panel 10. Resistance to upward pivoting of the extension panel results from the fact that the secondary lock is also engaged at this point. In particular, when the two body members 22 and 24 are locked together as shown in FIGS. 5A and 5B, the pivotable button 34 is flush with the top surface of the frame 50, whereupon each lever 80 is in its retracted position, as best seen in FIG. 5B. Since, each latch 68 is naturally biased by its spring 96 to pivot in the counter-clockwise direction in FIG. 5B, retraction of the associated lever 80 enables the associated latch to pivot to its "locked" position. Accordingly, the two projecting portions 38A of the frame 26 will be disposed within the mouths 68B of the two latches 68. Thus, if an upward force is applied to the extension panel, such as shown by the curved arrow designated by the reference letter "U" in FIG. 6A, the extension panel and the body member 24 to which it is secured will be prevented from pivoting upward more than a minimal amount, e.g., a few degrees. In such a case the primary lock, i.e., the locking action provided by the engaging surfaces 58 with the recesses 90 and receipt of the bosses 42 and 44 within their respective apertures 92 and 94 will not be disconnected.

To release the extension panel 12 from the patient support panel 10, the button 34 is depressed at the portion 34A to pivot it downward against the bias of the spring 76 to the position shown in FIGS. 7A and 7B. This pivoting action of the button 34 causes its link 84 to pivot in the clockwise direction as shown in FIG. 7B. The pivoting of the link is coupled by the pins 86 to the yoke 80A of each of the levers 80, thereby carrying both levers to the left, whereupon each lever's mesa portion 80B is disposed within the associated recess 88 in the upper portion of each recess 40 of the frame 26. In particular, the tapered surface 80C at the free end of each lever 80 will start to bear on the tip portion 68A of the associated latch 68, thereby causing the latch to begin to pivot in the clockwise direction against the bias of its associated spring 96. This action also seats and holds the mesa portions 80B of the levers 80 in their respective recesses 88 (called the "stowed state"). At this point everything is static because the upward pressure that the latch provides on the free end of the lever keeps the mesa end of the lever in its associated recess, thereby overcoming the bias that the spring 76 of the button applies to the button. Thus, the user can release pressure on the button, yet the button will stay in the released state shown in FIGS. 7A and 7B (at this point operation of the release mechanism becomes hands-free).

The user may then further lift the extension panel in the direction of the curved arrow U in FIGS. 8A and 8B to move to the next release stage (i.e., release stage 2). In this stage, the tapering surface 80C of each lever 80 will cause the tip 68A of the associated latch 68 to ride along it, thereby pivoting both latches further in the clockwise direction. This action frees the projections 38A from the mouths 68B of the latches 68, thereby releasing the secondary lock. However, the engagement of the tip 68D of each lever on the surface 80C of the associated lever caused by the bias of the associated spring 96 still applies an upward force to the free end of the lever, thereby holding the associated lever 80 in its stowed state. The surface 58 of each tab 56 will still be in engagement with its associated recess 90 in the frame 26, while the bosses 42 and 44 will be retracted somewhat from their respective recesses 92 and 94, so that the primary lock of the joint assembly will not be fully released at this point.

Further upward lifting of the extension panel as indicated by the arrow U in FIGS. 9A and 9B brings the disconnection of the panels to the next release stage, i.e., release stage 3. In this stage the levers 80 are still in their stowed state, but the tips 68A of the latches 68 are abutting the free ends 80D of the levers, whereupon the latches are pivoted to their maximum clock-wise position, but still apply some force on the free ends of the levers to hold the levers in their stowed state.

The moment that the tip 68A of each latch is free of the free end of its associated lever caused by further upward lifting of the extension panel, the mesa end of the lever drops out of its associated recess 88, whereupon the bias provided by the spring 76 of the button 34, causes the button 34 to pivot in the counterclockwise direction. This action carries the levers 80 from their stowed state back to a retracted state, such as shown in FIGS. 10A and 10B (release stage 4). The plates 82 serve to provide support for the levers when the levers are released from their stowed state. When the body members 22 and 24 are in this stage of release, the surfaces 58 of the tabs 56 are still within respective recesses 90 in the frame 50 and portions of the bosses 42 and 44 are still within their respective recesses or apertures 92 and 94.

Continued upward lifting of the extension panel, such as shown in FIGS. 11A and 11B, brings the body members 22 and 24 to the next release stage, i.e., release stage 5, whereupon the surfaces 58 of the tabs 56 begin to ride out of their respective recesses 90 in the frame 50, and the bosses 42 and 44 are almost free of their respective apertures or recesses 92 and 94.

In order to achieve the complete release of the primary lock of the joint assembly, the user continues to lift up on the extension panel in the direction of arrow U in FIGS. 12A and 12B to bring the bodies 22 and 24 into what is called release stage 6. At this stage, the surfaces 58 at the ends of the tabs 56 are out of their respective recesses 90 in the frame 50, and the bosses 42 and 44 are free of their respective apertures or recesses 92 and 94. The extension panel 12 with joint assembly body member 24 can then be removed from the patient support panel 10.

Connection of the extension panel to the patient support panel is accomplished in the following manner. The extension panel 12 with the body member 24 is lifted by a user and juxtaposed with respect to the body member 22 connected to patient support panel 10 like shown in FIGS. 13A and 13B (called insertion stage 1) so that the tabs 56 are guided by the guide plates 48 into their respective cavities 46 in the frame 26 of the body member 22. At this point in time the pivotable button 34 is in its flush position because its spring 76 will have retracted the levers 80 to their retracted states shown in those figures. At that time the latches 68 are biased to their maximum counterclockwise orientation by their associated springs 96, with the front wall 62A of the retainer boxes 62 serving as a stop to hold the latches in that state. When the latches 68 are in this state their respective mouths 68B are oriented to be able to receive the projections 38A of the frame 50 when the body members are appropriately oriented, i.e., at a further step in the securement of the body members 22 and 24 together. The extension panel and connected body member can then be moved to the position shown in FIGS. 14A and 14B (insertion stage 2), whereupon the surfaces 58 on the ends of the tabs 56 are disposed under the recesses 90 in the frame 26 and the bosses 42 and 44 are adjacent their respective recesses 92 and 94. At the same time the leading edge portions of the latch 68 immediately below the mouth of the latch begin to engage portions 38A of the projection 38, thereby starting to pivot the latch in the clockwise direction, e.g., the upper front edge portion of the latch moves away from the front wall 62A of the retainer box. The extension panel and the connected body member 24 can then be moved with respect to the body member 22 to the next insertion state or stage, which is the same as the heretofore identified release stage 5 (FIGS. 11A and 11B). The extension panel and the connected body member can then be moved with respect to the body member 22 (e.g., inserted further and pivoted downward with respect to the plane of the patient support panel), which is the same as the heretofore identified release stage 4 (FIGS. 10A and 10B). Engagement of the secondary lock is fully automatic. To that end, continued insertion of the body member 24 into the body member 22 while applying a downward force on the extension panel to rotate in downward with respect to the plane of the patient support panel 10 will eventually bring the two body members to their locked state (i.e., the state shown in FIGS. 5A and 5B) wherein the body members 22 and 24 are automatically locked together by the weight and downward pressure provided by the extension panel 12 and the attached body member 24.

It should be pointed out at this juncture that the various components making up the joint assembly described heretofore are merely exemplary of various alternative components that can be used in accordance with this invention. For example, it is contemplated that the bosses and apertures for receiving the bosses may be reversed, e.g., the apertures or recesses 92 and 94 being located in the frame 26 of body 22 and the bosses 42 and 44 being located in the frame 50. Moreover, the bosses themselves can be of a different construction. For example, as shown in FIGS. 4G and 4H, the integral rectangular bosses 44 that control longitudinal and lateral play shown in FIG. 4A may be replaced with a pair of alternative bosses 44A, each constructed like the single one shown in FIG. 4G. The bosses 44A are arranged to be received in correspondingly shaped recesses or apertures 94A shown in FIG. 4H and are made of acetal. Each boss is mounted on the frame 26 by an associated screw 44B. Each boss 44A has an end geometry that is spring like to allow for a small interference between it and the rectangular recess or aperture 94A where it resides to ensure stability of the extension panel especially at the distal end.

Other changes can be made to the components of the joint assembly. For example, instead of the body member 22 being secured to the patient support panel and the body member 24 being secured to the extension panel, the body members can be reversed, i.e., the body member 22 being secured to the extension panel and the body member 24 being secured to the patient support panel. Moreover, instead of using redundant components, i.e., two levers 80 and associated latches 68, only one lever and one associated latch may be used. So too, only one tab and associated cavity for receiving it may be utilized, if appropriate. Moreover, the construction of the latch and the lever for moving the latch can be modified as desired, preferably so long as the mechanism for disengaging the latch operates when initiated to unlock the latch and to hold the mechanism in a stowed state. Further still the means for biasing for the latches and the pivotable button can be provided in other ways than shown. The actuator subassembly button, itself, may be replaced by a movable member that is not pivotable, so long as it is able to control the release of the secondary lock.

As should be appreciated by those skilled in the art from the foregoing the joint assembly and its associated patient support panel and extension panel provide a patient support structure that is easy to use and which eliminates potential failure either inadvertently or through operator error. To achieve those ends the joint assembly provides a simple intuitive connection mechanism that is self aligning when docking. Secondly post docking, with downward force on the extension (the removable portion), the joint solidly stabilizes and locks the two panels in relative alignment and level to (flush with) each other. Third, a fail-safe secondary lock mechanism is included, that restricts inadvertent separation of the two panels if upward forces are encountered. The simple locking mechanism is largely located within the body member of the patient support panel which is fixed on the pedestal 14, thus reducing the potential harm that could occur to it if the extension panel was to be dropped or mishandled.

The simple yet highly functional lock mechanism provided by the joint assembly provides several automatic operations starting with automatic engagement during docking of the extension panel to the patient support panel. When activated for release, this lock maintains the released position without further attention by the operator allowing the operator the opportunity to position both hands as best desired to securely grasp the extension panel for removal and handling. Importantly the lock mechanism provides this disengagement function without requiring displacement or movement of the removable extension panel. By not displacing or moving the extension panel when releasing the lock (or requiring external support such as may be provided by an operator) the subject invention avoids any need for a support beam or beams or a highly leveraged release mechanism that would otherwise be needed to offset the forces inherent in the preferred cantilevered configuration (no support beams) while not sacrificing the advantageous automatically locking feature when docking.

The locking mechanism is additionally designed to automatically reset itself when the extension panel is removed so that it is always ready to automatically lock the next docked extension. If the operator should decide not to remove the extension panel after activating the lock release he/she may easily reactivate it by manually pressing the release lever back into the lock position (flush with the patient support panel top). For further insurance that the lock is always ready to automatically secure the next extension panel when docked it is designed such that it will not stay in the unlocked or released position except when an extension is in place (short of the operator secondarily holding the lever in the release position). This eliminates any potential failure that may arise due to an operator inadvertently disengaging the lock without an extension in place and forgetting to return it to the lock position.

Additionally the lock mechanism button is centrally located in the assembled components such that when in the released position it extends above the top surface in the path of the patient making it obvious visually and physically that the locking mechanism is disengaged. Being located under the patient also renders inadvertent release with a patient on board highly unlikely.

Without further elaboration the foregoing will so fully illustrate my invention that others may, by applying current or future knowledge, adopt the same for use under various conditions of service.

We claim:

1. A joint assembly for releasably connecting an extension panel to a patient support panel mounted on a pedestal, the patient support panel defining a first plane, the extension panel defining a second plane, said joint assembly comprising a first body member and a second body member, one of said first and second body members being arranged to be secured to the patient support panel and the other of said first and second body members being arranged to be secured to the extension panel, said first body member comprising an actuator subassembly and a frame including a projection, a first locking member and an overhang having an undersurface with a first recess therein, said second body member comprising a movable latch and a frame including at least one tab member and a second locking member, said second body member with said extension panel secured thereto being configured to be brought into engagement with said first body member so that said first and second planes extend at an obtuse angle with respect to each other, whereupon said second body member is configured to pivot with respect to said first body member during abutting engagement between said first locking member and said second locking member so that said first and second planes are parallel to each other when said first body member and said second body member are locked together, whereupon a portion of said at least one tab member is releasably received within said first recess and with said first and second locking members engaging each other to lock said first and second body members together to prevent downward movement of the extension panel with respect to the patient support panel, and with said latch of said second body member engaging said projection of said first body member to lock said first and second body members together and thereby prevent upward movement of the extension panel with respect to the patient support panel.

2. The joint assembly of claim 1 wherein said joint assembly self aligns, self levels, is immediately stable and locks automatically by the weight and downward pressure on said second body member when said first and second body members are connected together.

3. The joint assembly of claim 1 wherein said actuator subassembly comprises a manually movable button whose operational position visually indicates if the joint is locked or unlocked.

4. The joint assembly of claim 1 wherein said actuator subassembly is arranged for moving said latch to release said latch from engagement with said projection, whereupon said second body member with said extension panel secured thereto can be tilted upward with respect to said first body member to free said portion of said at least one tab member from said recess and to cause said first and second locking members to disengage from each other and thereby unlock said first and second body members from each other.

5. The joint assembly of claim 1 wherein said movable latch is arranged to be pivoted about an axis in a first rotational direction to releasably engage said projection of said first body member.

6. The joint assembly of claim 5 wherein said latch is normally biased by a spring in said first rotational direction.

7. A patient support table comprising said joint assembly, said patient support panel and said extension panel as set forth in claim 1.

8. The patient support table of claim 7 wherein the patient support table is a radiation therapy treatment table.

9. The patient support table of claim 8 wherein said patient support panel includes at least one component enabling said patient support panel to be secured to the pedestal.

10. The patient support table of claim 8 wherein the patient support panel and the extension panel are each formed of a carbon composite.

11. The patient support panel of claim 9 wherein said patient support panel and said extension panel are each formed of a carbon composite.

12. The patient support table as set forth in claim 8 wherein said actuator assembly comprises a manually movable button whose operational position visually indicates if the joint is locked or unlocked.

13. The joint assembly of claim 1 wherein said second body member must pivot with respect to said first body member during engagement between said first locking member and said second locking member.

14. The joint assembly of claim 1 wherein said second body member is configured to pivot with respect to said first body member during disengagement between said first locking member and said second locking member.

15. The joint assembly of claim 1 wherein said movable latch is distinct from said second locking member.

16. The joint assembly of claim 1 wherein said first locking member is spatially separate from said projection.

17. A joint assembly for releasably connecting an extension panel to a patient support panel mounted on a pedestal, the patient support panel defining a first plane, the extension panel defining a second plane, said joint assembly comprising a first body member and a second body member, one of said first and second body members being arranged to be secured to the patient support panel and the other of said first and second body members being arranged to be secured to the extension panel, said first body member comprising an actuator subassembly and a frame including a projection, a first locking member and an overhang having an undersurface with a first recess therein, said second body member comprising a movable latch and a frame including at least one tab member and a second locking member, said second body member with said extension panel secured thereto being configured to be brought into engagement with said first body member so that said first and second planes extend at an obtuse angle with respect to each other, whereupon said second body member is configured to pivot with respect to said first body member so that said first and second planes are parallel to each other, whereupon a portion of said at least one tab member is releasably received within said first recess and with said first and second locking members engaging each other to lock said first and second body members together to prevent downward movement of the extension panel with respect to the patient support panel, and with said latch of said second body member engaging said projection of said first body member to lock said first and second body members together and thereby prevent upward movement of the extension panel with respect to the patient support panel, wherein said first locking member comprises a boss and wherein said second locking member comprises a second recess for releasable receipt of said boss.

18. A joint assembly for releasably connecting an extension panel to a patient support panel mounted on a pedestal, the patient support panel defining a first plane, the extension panel defining a second plane, said joint assembly comprising a first body member and a second body member, one of said first and second body members being arranged to be secured to the patient support panel and the other of said first and second body members being arranged to be secured to the extension panel, said first body member comprising an actuator subassembly and a frame including a projection, a first locking member and an overhang having an undersurface with a first recess therein, said second body member comprising a movable latch and a frame including at least one tab member and a second locking member, said second body member with said extension panel secured thereto being configured to be brought into engagement with said first body member so that said first and second planes extend at an obtuse angle with respect to each other, whereupon said second body member is configured to pivot with respect to said first body member so that said first and second planes are parallel to each other, whereupon a portion of said at least one tab member is releasably received within said first recess and with said first and second locking members engaging each other to lock said first and second body members together to prevent downward movement of the extension panel with respect to the patient support panel, and with said latch of said second body member engaging said projection of said first body member to lock said first and second body members together and thereby prevent upward movement of the extension panel with respect to the patient support panel, wherein said movable latch is arranged to be pivoted about an axis in a first rotational direction to releasably engage said projection of said first body member, said latch is normally biased by a spring in said first rotational direction, and said actuator assembly comprises a lever having a free end arranged to be moved to an extended position engaging said latch to pivot said latch about said axis in a second rotational direction, opposite said first rotational direction, to release said latch from engagement with said projection of said first body member.

19. The joint assembly of claim 18 wherein said actuator assembly comprises a pivotable button coupled to said lever and arranged when depressed at a first point on said button to pivot said button in a first rotational direction to move said lever to said extended position.

20. The joint assembly of claim 19 whereupon said release of said projection from said hook enables said second body member with said extension panel secured thereto to be tilted upward with respect to said first body member to free said portion of said at least one tab member from said recess and to cause said first and second locking members to disengage from each other, to thereby unlock said first and second body members from each other, whereupon said second body member with said extension panel secured thereto can be removed.

21. The joint assembly of claim 20 wherein said button is normally biased by a spring to pivot said button in a second rotational direction, said second rotational direction being opposite to said first rotational direction.

22. The joint assembly of claim 21 wherein said free end of said lever includes a surface arranged to engage a correspondingly shaped surface of said projection when holding said lever in said extended position.

23. The joint assembly of claim 22 wherein said latch bearing against said lever in said extended position holds said surface of said lever in engagement with said correspondingly shaped surface of said projection against the bias provided on said button provided by said spring.

24. The joint assembly of claim 22 wherein said latch is arranged to be moved to a position not bearing on said lever, whereupon said spring biasing said button causes said surface of said lever to become disengaged from said correspondingly shaped surface of said projection, whereupon said lever moves to a retracted position.

\* \* \* \* \*